United States Patent
Wilson et al.

(10) Patent No.: US 8,491,473 B2
(45) Date of Patent: Jul. 23, 2013

(54) MEDICAL PROCEDURE MAT AND DRAPING SYSTEM

(75) Inventors: Robert F. Wilson, Roseville, MN (US); Robert Kim, Shoreview, MN (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 889 days.

(21) Appl. No.: 12/526,167

(22) PCT Filed: Feb. 8, 2008

(86) PCT No.: PCT/US2008/053366
§ 371 (c)(1), (2), (4) Date: Sep. 19, 2009

(87) PCT Pub. No.: WO2008/098152
PCT Pub. Date: Aug. 14, 2008

(65) Prior Publication Data
US 2010/0324433 A1 Dec. 23, 2010

Related U.S. Application Data

(60) Provisional application No. 60/888,810, filed on Feb. 8, 2007.

(51) Int. Cl.
*A61B 5/0402* (2006.01)
(52) U.S. Cl.
USPC .......................... 600/301; 600/508; 600/509
(58) Field of Classification Search
USPC ...... 5/600, 607–611, 694, 904, 940; 600/301, 600/508, 509
See application file for complete search history.

(56) References Cited

U.S. PATENT DOCUMENTS

| | | | |
|---|---|---|---|
| 4,595,023 A | 6/1986 | Bonnet | |
| 4,841,587 A * | 6/1989 | Carter et al. | 5/419 |
| 5,006,718 A | 4/1991 | Lenhart | |
| 5,733,247 A | 3/1998 | Fallon | |
| 5,964,703 A | 10/1999 | Goodman et al. | |
| 6,314,959 B1 | 11/2001 | Griesbach et al. | |
| 6,425,878 B1 * | 7/2002 | Shekalim | 604/65 |

(Continued)

FOREIGN PATENT DOCUMENTS
WO 2004045407 A1 6/2004

OTHER PUBLICATIONS

"PCT International Search Report dated May 19, 2008, from which the instant application is based," 2 pgs.

(Continued)

*Primary Examiner* — Deborah Malamud
(74) *Attorney, Agent, or Firm* — Fredrikson & Byron, P.A.

(57) ABSTRACT

A medical procedure mat for supporting a patient. A mat having a cushioned substrate and one or more physiological monitoring lines, the physiological monitoring lines having guided portions along the outer edge of the cushioned substrate, and flexible portions operatively coupled to the guided portions, the flexible portions being adapted to extend toward the patient. A draping system for use during medical procedures, including a top and/or bottom drape. A bottom drape including an absorbent material and/or a privacy shield. A top drape including a workbench surface. A mat and draping system in which a bottom and top drape mate to each other and/or to the mat. A draping system providing openings or holes to allow passage of one or more physiological monitoring lines when used in conjunction with the mat.

36 Claims, 12 Drawing Sheets

U.S. PATENT DOCUMENTS

| | | |
|---|---|---|
| 6,493,568 B1 | 12/2002 | Bell et al. |
| 7,096,870 B2 | 8/2006 | Lamprich et al. |
| 8,013,750 B2 * | 9/2011 | Sandholdt ............... 340/626 |
| 2003/0033675 A1 * | 2/2003 | Solesbee et al. ............ 5/694 |
| 2004/0111045 A1 * | 6/2004 | Sullivan et al. ............ 600/595 |
| 2007/0017030 A1 * | 1/2007 | Salt et al. ................. 5/621 |
| 2010/0231377 A1 * | 9/2010 | Sandholdt ............... 340/539.1 |

OTHER PUBLICATIONS

"PCT Written Opinion dated May 19, 2008, from which the instant application is based," 5 pgs.

\* cited by examiner

MEDICAL PROCEDURE MAT AND DRAPING SYSTEM

RELATED APPLICATIONS

This application is a 35 U.S.C. 371 national stage filing from International Application No. PCT/US2008/053366 filed Feb. 8, 2008, which claims priority to U.S. Provisional Patent Application No. 60/888,810, filed Feb. 8, 2007, the teachings of which are incorporated herein by reference.

TECHNICAL FIELD

The present application relates generally to the use of devices during medical procedures (e.g., heart catheterization, surgery, medical imaging) in which a patient lies on a surface.

BACKGROUND

During medical procedures, patients often lie on a surface and are hooked by wires or cables to a variety of medical devices. The cables often can become tangled or detached. During these procedures, patients often lie on foam mats that are not comfortable and are cold. Arm boards to support the arms are usually detachable from the table, but when they are detached, they can fall to the ground or otherwise get in the way. After procedures, patients need to be lifted off of the mats and transferred to beds or other transport devices.

In addition, the mats typically need to be draped to avoid contamination from patient to patient. The drapes are often simple sheets of paper or polymer material, and they may have pockets sewn in. Patients may need to urinate during prolonged procedures, but in order to do so, they either urinate on themselves and the drape (resulting in a pool of fluid) or they need to have a urinal or catheter placed by ancillary personnel.

Typically, the mat stays with the table from procedure to procedure, and is often uncomfortable. After lying on the mat for a prolonged period of time, a patient may begin to experience back or neck pain. The use of cables may also become cumbersome or inefficient. Because many types of cables, tubes, lines, and the like may need to be used (such as for ECG (electrocardiogram), NIBP (non-invasive measurement of blood pressure), SaO2, or O2), they may become cumbersome to attach, or may be caught on certain large equipment components (such as X-ray equipment). This could prolong setup and procedure time.

Also, in many current medical procedures, medical personnel place their tools on a cart behind them and pull the tools they need onto the drape that covers the patient. Tools often fall on the floor. Some tasks, such as holding a catheter or guidewire for a doctor, require the presence of additional personnel, which is wasteful and inconvenient.

BRIEF SUMMARY

Various embodiments of the present invention are provided in the accompanying description and attachments. In one embodiment, a mat is provided for patients to lie on during medical procedures. The mat may have one or more of the following components or features: wiring for lead attachments (such as for ECG (electrocardiogram)); inflatable or moveable back supports; an entertainment and communication system; an integrated heating/cooling system; piping for oxygen; wiring for other medical devices (such as SaO2 sensors); and/or integrated medical devices such as those intended to pump fluid or monitor Doppler flow.

In one embodiment, a sterile draping system with an integrated absorbent material is provided that will absorb urine (or other biological fluids) and/or procedure fluids (e.g., contrast solution, saline). The sterile draping system may include a flap that forms a "privacy shield" to cover body parts, and/or an integrated set of containers and fasteners to hold medical equipment during medical procedures.

The details of one or more embodiments of the invention are set forth in the accompanying drawing figures and the description below. Other features, objects, and advantages will be apparent from the description and attachments. The embodiments shown and described are provided for the purposes of illustration, not limitation.

DESCRIPTION

Figure 1B:
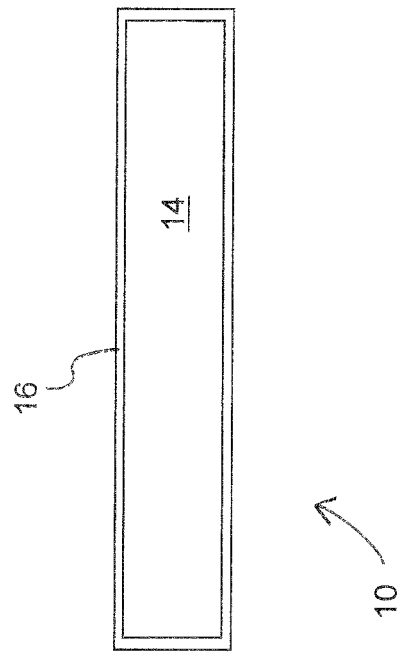
FIG. 1b is a cross-sectional view of a medical procedure mat having detachable arm supports.

Various exemplary embodiments are described herein with reference to the accompanying drawing figures in which like numbers describe like elements.

In one embodiment, a mat is provided that includes wiring, cabling, heating, cooling, grip rings, integrated devices, and/or other features. In one embodiment, a patient draping system is provided that addresses the problem of urination, and that further forms a workbench for the medical personnel. The draping system may include clips to hold wires and catheters, and may further include storage for equipment not in use. In one embodiment, the use of such a mat and/or patient draping system may help improve medical procedure efficiency by reducing procedure delays and interruptions, reducing the amount of material that may potentially fall off the table, reducing the number of personnel needed for procedures, and/or improving patient comfort.

One embodiment of a medical procedure mat may include wiring, tubes, or other lines (e.g., physiological monitoring lines) for various components, such as for the monitoring of ECG (electrocardiogram), NIBP (non-invasive measurement of blood pressure), SaO2, or O2. The medical procedure mat may stay with the patient from the medical room (such as an operating room or cardiac catheterization lab) into a recovery area, according to some embodiments of the invention. In some embodiments, the mat may have side grips for moving the patient to a gurney. In addition, one or more drapes, or a draping system, may be used in conjunction with the mat, and may be further adapted to mate to the mat in some embodiments. The drape may have a top layer that forms a workbench, and a bottom layer having an absorbent material, a privacy shield, and support for the workbench. In one embodiment, the mat may stay in the medical procedure room and does not necessarily move with the patient.

In one embodiment, cable and tubing management are provided. Quick connects and other connectors (such as reel connectors) may be provided for ECG, NIBP, SaO2, or other types of physiological monitoring lines. This embodiment may provide various advantages or benefits, such as faster throughput (allowing quicker patient hook-up time), or minimization of case disruption while cables or connectors are re-routed.

In one embodiment, an advanced workbench drape is provided that may include a wire or balloon storage, a workbench tool set, wire/catheter stabilization devices, and an absorbent material with a privacy flap. This embodiment may provide various advantages or benefits, such as improved efficiency, and reduction of case delay and complications from urine management or bladder catheterization. In addition, one individual may be able to perform catheter movements previously achievable only with involvement from two individuals.

In one embodiment, a patient comfort feature is provided. This feature may include neck or back supports, heating of the mat, and/or music with patient control. This embodiment may provide various advantages or benefits, such as increased patient loyalty and comfort. In one embodiment, a communication feature may also be provided for improved efficiency or enhanced communication. Headsets for personnel or patients may also be included.

A medical procedure mat and draping system may include a work surface, according to one embodiment of the present invention. Various features of such a system are described for the mat and draping system, which may be referred to herein as "iMAT" (integrated mat). The mat may include one or more of the following features: a raised comfort perimeter; an integrated wiring harness (for wiring and/or other connections); a wearable ambient device (such as headphones, which may be used by a patient when lying down on the mat, and which may have a wireless interface); a grab handle; a head/neck rest; an ECG wire spool or reel; a shoulder/ribcage pad; a movable padded arm rest; a movable lumbar with tailbone pad; an accessible plug port; a heat source (which may be driven electrically or by forced air, for example); a cable pass-through (for passing cables from one end of the mat to the other; and/or a removable lower portion.

The work surface of the iMAT system may include one or more of the following features: a pivoting arm that can be used to move a work surface over the table and mat, a removable tray, a removable fluid (e.g., saline) container, a removable storage container, lids, and/or an energy (e.g., light) source.

A drape or draping system may be used alone or in conjunction with the medical procedure mat described herein. Various features are described for a top and a bottom drape, and for an integrated draping system, which may be referred to herein as "iDRAPE" (integrated drape). A drape or draping system according to embodiments of the invention may include one or more of the following features: a heat source (which may be driven electrically or by forced air, for example), a "modesty" panel to shield/hide/mask/etc. one or more portions of a patient's body, integrated absorbent briefs (to absorb bodily fluids, for example), adhesive pass thrus (for attaching to the patient), drape material (which may be transparent), perforated pass thrus (for passing through equipment or other components, for example), and an integrated bottom drape. In one embodiment, a top drape and a bottom drape are not integrated, but are attachable or connectable.

Figure 1A:
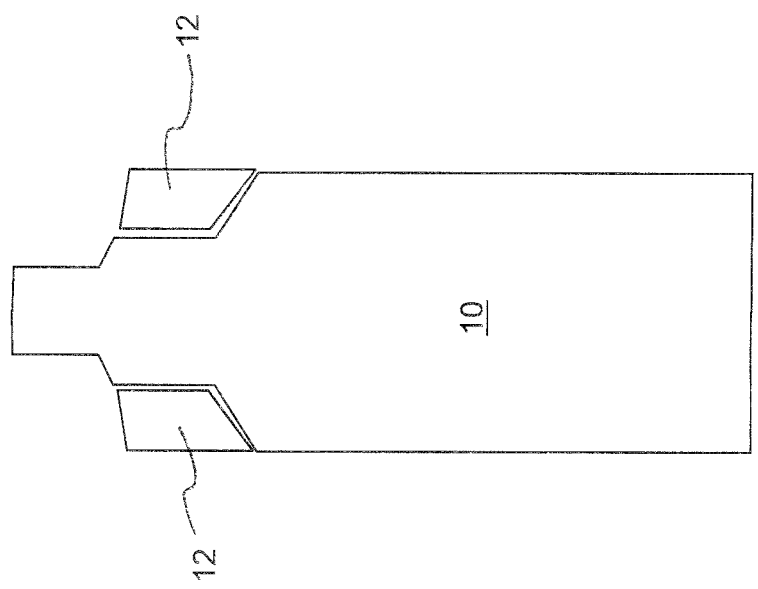
FIG. 1a is a top view of a medical procedure mat having detachable arm supports.

FIG. 1a is a top view of a medical procedure mat 10 having detachable arm supports or boards 12, as are known in the art. The medical procedure mat 10 is typically a foam mat, comprising a cushioned substrate 14 and/or a radiolucent material 12 covering the cushioned substrate 14, as is shown in the cross-sectional view of mat 10 shown in FIG. 1b.

Figure 2:
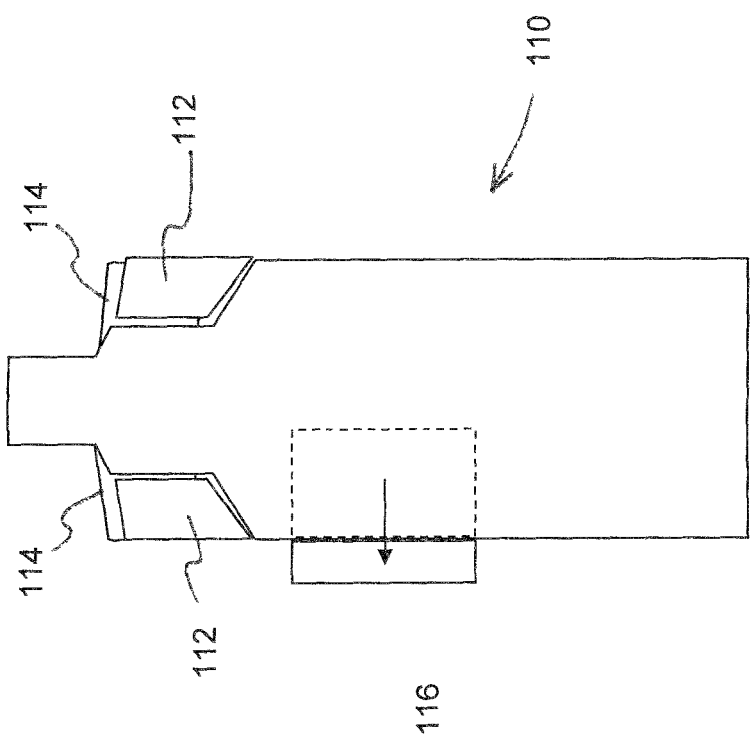
FIG. 2 is a conceptual top view of a medical procedure mat having integral armrests, according to one embodiment.

FIG. 2 is a conceptual top view of a medical procedure mat 110 having integral armrests 112, according to one embodiment. The armrests 112 are integral and attached to the mat 110, but they also may be slid or moved (e.g., rotated or angled down) by an operator for optimal positioning or comfort. In some embodiments, the armrests 112 may be operatively coupled to arm boards 114, which may provide additional options for positioning the armrests 112. For example, the arm boards 114 may be pivotally coupled to the mat 110 to allow the arm boards 114 and the arm rests 112 to be placed in a stowed position. Because the armrests 112 and arm boards 114 are integral to the mat 110, they do not need to be detached from the mat 110. They may be stored in or beside the mat 110, or underneath the mat 110, according to some embodiments of the invention. The armrests 112 and/or arm boards 114 may also include integrated NIBP or SaO2 sensors according to certain embodiments of the invention.

FIG. 2 also shows radiation shield 116, which may be incorporated in a medical procedure mat 110 according to certain embodiments of the invention. The medical procedure mat 110 includes a cushioned substrate having a top surface (for supporting a patient lying on the mat), a bottom surface that can be positioned on and supported by a medical procedure table, an inner portion, and an outer edge portion that includes sections generally corresponding to the outer periphery of the cushioned substrate, adjacent the head, foot, left and right sides of the patient, for example. The radiation shield 116 may be disposed along the outer edge portion of the cushioned substrate, and may be positioned to reduce scattering radiation received by an operator during a patient imaging procedure. In some embodiments, the radiation shield 116 may be positionable between a stowed position (indicated by dotted lines in FIG. 2) and a shielding position (indicated by solid lines in FIG. 2). The arrow might indicate, for example, that the radiation shield 116 is pulled out from the mat 110, and is then positioned (e.g., generally vertically) to provide protection from scattering radiation. In some embodiments, a second radiation shield (not shown) may also be employed (e.g., one radiation shield 116 disposed on the left side of the outer edge portion, and the second radiation shield 116 disposed on the right side of the outer edge portion, both shields being positionable (e.g., by medical staff personnel) between a stowed position and a shielding position.

FIGS. 3a through 3d are conceptual diagrams of a medical procedure mat 110 incorporating one or more physiological monitoring lines (e.g., electrocardiogram or "ECG" cables, blood pressure monitoring lines, oxygen saturation monitoring, etc.), according to one embodiment. The medical procedure mat 110 includes a cushioned substrate having a top surface (for supporting a patient lying on the mat), a bottom surface that can be positioned on and supported by a medical procedure table, an inner portion, and an outer edge portion that includes sections generally corresponding to the head, foot, left and right sides of the patient.

Figure 3B:
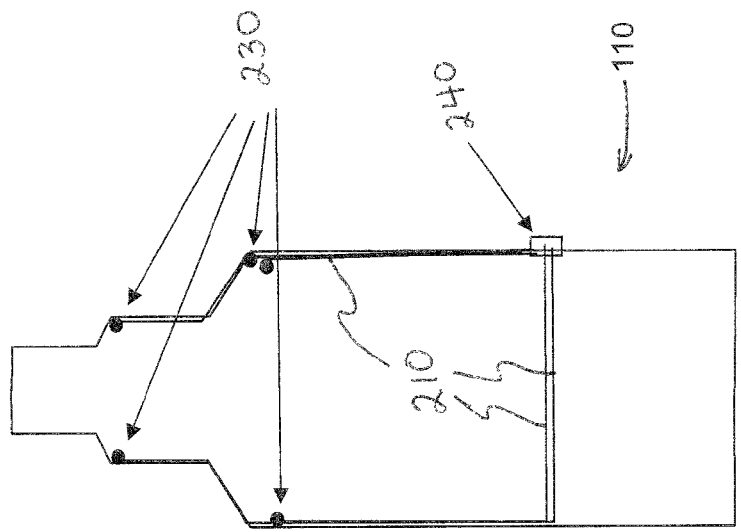
FIGS. 3a-3d are conceptual diagrams of a medical procedure mat incorporating physiological monitoring lines, according to one embodiment.
Figure 3A:
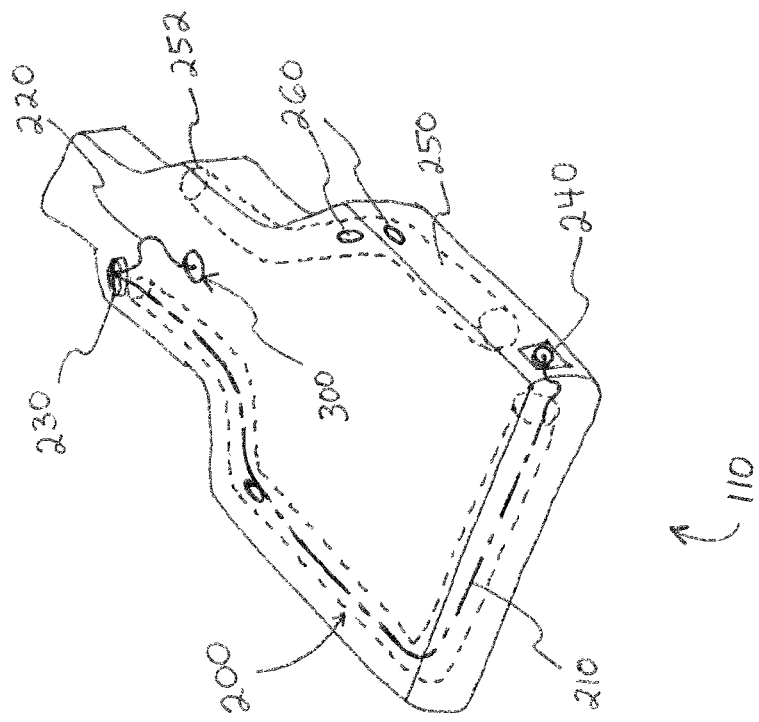

As shown in FIG. 3a, the mat 110 further includes at least one physiological monitoring line 200, which is capable of communicating a physiological signal from a physiological sensor 300 associated with the patient (not shown). The physiological monitoring line 200 includes a guided portion 210 having a proximal end and a distal end, a flexible portion 220, and an operative coupling 230 between the distal end of the guided portion 210 and the flexible portion 220. As shown in FIG. 3a, the operative coupling 230 may be disposed generally near the outer edge portion of the cushioned substrate, and may be adapted to retract or retrieve the flexible portion 220. The guided portion 210 may be disposed along the outer edge portion of the cushioned substrate. For example, the guided portion 210 shown in FIG. 3a follows the contour of the outer edge portion along the foot, right side, and toward the head of the outer edge portion. The positioning of physiological monitoring lines in this manner provides benefits during imaging procedures (e.g., x-ray or other comparable procedures) that may include keeping the physiological monitoring line 200 out of the imaging area of interest, and avoiding having the physiological monitoring lines interfere with movement of imaging equipment and/or personnel about the procedure table.

The proximal end of the guided portion 210 of the physiological monitoring line 200 can be adapted to facilitate connection to a monitoring device, according to some embodiments of the invention. For example, as shown in FIG. 3a, the proximal end of guided portion 210 terminates at a hub 240 that may allow for convenient connections between one or more physiological monitoring lines and one or more external monitoring devices.

The flexible portion 220 may be adapted to extend toward the inner portion of the cushioned substrate. This may be useful, for example, to facilitate connection or coupling to the physiological sensor 300 associated with the patient. In some preferred embodiments, the flexible portion 220 may remain substantially refracted (e.g., near or within the operative coupling 230) until a patient is situated on the top surface of the cushioned substrate. At that point, a medical staff person may couple the flexible portion 220 to the physiological sensor 300 by extending the flexible portion 220 and coupling it (e.g., by connecting, attaching, or placing in proximity) to the physiological sensor 300.

The physiological monitoring lines 200 may be adapted to communicate electrical signals (as would be the case with ECG signals, for example), or may be adapted to communicate fluid signals (e.g., blood pressure signals, or oxygen saturation signals). FIG. 3b is a top plan view of one particular embodiment of the invention in which there is at least a second physiological monitoring line, the physiological monitoring lines in this particular example comprising a number of ECG cables. For example, FIG. 3b illustrates an embodiment of the invention in which five ECG cables are incorporated as the physiological monitoring lines 200 of the medical procedure mat 110. Thus, in the embodiment illustrated, each of the five ECG cables includes guided portions 210 and operative couplings 230 disposed generally near the outer edge portion of the cushioned substrate of mat 110. In some embodiments, the operative couplings 230 may be positioned on an outside surface of the cushioned substrate. Although not shown in FIG. 3b, flexible portions 220 would typically extend from the operative couplings 230 to facilitate connections with ECG sensors (e.g., surface electrodes) placed on the patient's skin. The proximal ends of the guided portions 210 may be coupled together at hub 240, which may, for example, allow for the connection of some or all of the ECG cables to an external monitor with a single connection.

Hub 240 may, for example, facilitate connection of physiological monitoring lines 200 to a monitoring device. In some embodiments, hub 240 may include more than one type of connector, for example, to allow for connection of different types of physiological monitoring lines to different types of monitors. One type of connector, for example, could be a multi-pin connector for electrically coupling ECG cables to an ECG monitor. Another type of connector could be a tubing connector (e.g., luer connector) adapted to couple a fluid signal (e.g., a blood pressure monitoring line, or an oxygen saturation monitoring line) to an appropriate monitoring device.

In one embodiment, the operative couplings 230 may comprise reel connectors that can be extended and retracted quickly and effectively. In one embodiment, the connectors may comprise coil connectors that may also be capable of being extended and retracted quickly and effectively. Such reel or coil connectors may include a housing as part of the operative coupling 230 into which the flexible portion 220 of the physiological monitoring line 200 may be retracted. In some embodiments, the operative couplings 230 are adapted to place a tension on the flexible portion 220, which effectively pulls the flexible portion 220 toward the operative coupling 230. The arrangement of physiological monitoring lines as described above (ECG "line piping") with reel connectors or coil connectors may allow faster connections to be made, and may also help minimize the number of times medical personnel need to re-attach or re-route cables during medical procedures. The use of the connectors may help minimize cable interference with X-ray C-arms, for example, or may also minimize lead pull-offs. For example, the operative couplings 230 may include a detent position that allows an operator to selectively remove the tension on the flexible portion 220 (for example, once the flexible portion 220 is connected to the physiological sensor 300 and any slack is taken out of the flexible portion); this might decrease the likelihood of the physiological sensor 300 being pulled off of the patient by the tension supplied by the operative coupling 230. The locations, positions, and types of connectors shown in FIGS. 3a-3d are provided by way of example and are for illustrative purposes only. In different embodiments, various different locations, positions and/or types of connectors may be used.

Figure 3D:
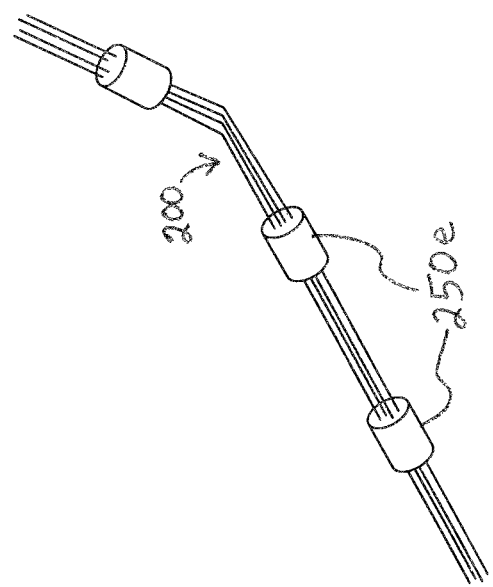
Figure 3C:
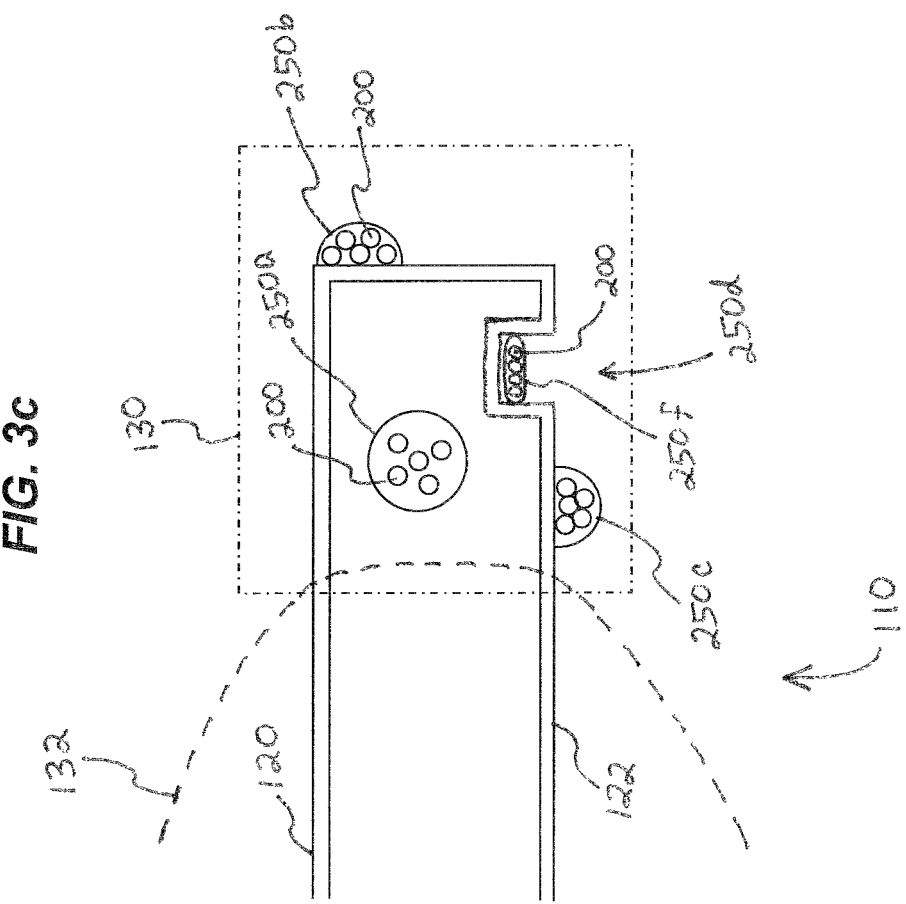

FIG. 3c is a partial, cut-away cross-sectional view of a medical procedure mat 110 according to various embodiments of the invention. FIG. 3c illustrates the general arrangement of portions of mat 110, including the top surface 120, bottom surface 122, inner portion 132, and outer edge portion 130. In some embodiments, a conduit 250 may be employed to guide the guided portions 210 of one or more physiological monitoring lines 200 along the outer edge portion 130 of the cushioned substrate. In such embodiments, one or more physiological monitoring lines 200 may be housed within a conduit 250 disposed along or within the outer edge portion 130. FIG. 3c shows several types of conduits 250 which may be employed according to various embodiments of the invention. For example, conduit 250 may be disposed within the cushioned substrate, substantially as illustrated by conduit 250a. Alternately, conduit 250 may be disposed outside the cushioned substrate, and may include, for example, generally semi-circular members such as those illustrated at 250b and 250c. In one embodiment, conduit 250 may comprise a hollow space formed in the cushioned substrate, and could include, for example, the conduit illustrated at 250d in FIG. 3c. A further embodiment shows conduit 250f comprising a ribbon-type cable, as are know in the art, and which may include a plurality of physiological monitoring lines 200 encased in a substantially flat, flexible, non-conducting material. In FIG. 3c, conduit 250f is shown disposed within hollow space conduit 250d, but both types of conduits could be used independently of each other according to embodiments of the invention.

FIG. 3d shows another possible embodiment of a conduit 250. For example, conduit 250e in FIG. 3d comprises two or more discontinuous portions adapted to guide the guided portions 210 of one or more physiological monitoring lines 200. For example, two or more discrete "bands" may be spaced along the outer edge portion of the cushioned substrate to guide the physiological monitoring lines 200, as shown in FIG. 3d. This may have the advantage of reducing the total weight of the medical procedure mat 110, and may also provide enhanced imaging characteristics. For example, the discrete bands 250e may be less likely to show up on an x-ray. Alternately, depending on the material used, the bands may serve as radiopaque markers to show relative locations and/or distances, for example.

In some embodiments of the invention, the conduit 250 is a generally annular member that extends along the outer portion of the cushioned substrate. The generally annular member may typically be elongate and hollow, and may be substantially tubular or cylindrical in cross-section, for example, but could also be semi-circular or "C"-shaped in cross-section as well. In one embodiment, for example, the generally annular member is substantially tubular with a longitudinal slit or gap to allow for the addition or removal of physiological monitoring lines 200 to/from conduit 250.

With reference back to FIG. 3a, the conduit 250 may be an annular member having a distal opening 252 located near an operative coupling 230 corresponding to one of the physiological monitoring lines 200. In some embodiments, the annular member may further include one or more side openings 260 as shown in FIG. 3a. Each of the side openings may, for example, be positioned to allow for coupling (e.g., via the operative couplings 230) between the guided portion 210 and the flexible portion 220 of one of the physiological monitoring lines 200 according to certain embodiments. The outer edge portion may additionally include one or more side holes that extend from inside the cushioned substrate to outside the cushioned substrate. In certain other embodiments, the annular member may be a tube adapted to bend to conform to the shape of the outer edge portion of the cushioned substrate. In yet another embodiment, the conduit may comprise a tube disposed within a hollow space formed in the cushioned substrate, the tube having one or more side openings that can be generally aligned with side holes in the cushioned substrate; such an arrangement would allow the physiological monitoring lines to be routed from a position within the tube, through the side holes in the cushioned substrate, to a location outside the cushioned substrate.

In one particularly preferred embodiment of the invention, the medical procedure mat 110 includes two conduits: a first conduit running generally along the left side of the outer edge portion, and a second conduit running generally along the right side of the outer edge portion, each of the conduits being capable of guiding at least one physiological monitoring line between an area near the foot and an area near the head of the outer edge portion. In one example of such an embodiment, the guided portion of one of the physiological monitoring lines runs from the left side to the right side near the foot of the outer edge portion.

Figure 4:
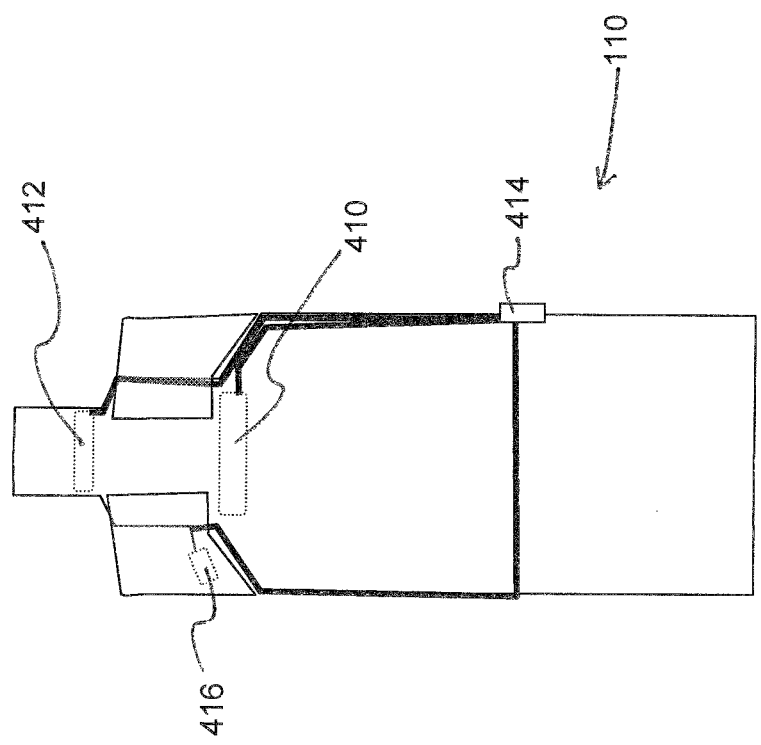
FIG. 4 is a conceptual top plan view of a medical procedure mat having neck and back supports, according to one embodiment.

FIG. 4 is a conceptual top plan view of a medical procedure mat 110 having neck and back supports, according to one embodiment. In this embodiment, an air pump 414 is provided on a side of the mat 110 to supply air to one or more neck or back support mechanisms. As shown in FIG. 4, air bags for a low back support 410 and a neck support 412 are provided. In some embodiments, there may also be a neck and back support controller 416. In one embodiment, a user (such as a patient or a medical staff professional) may manipulate the air pump 414 using the controller 416 to control the amount of air supplied to the neck support 412, and/or may control the nature or amount of the support provided by the low back support 410. These mechanisms help improve patient comfort.

Figure 5:
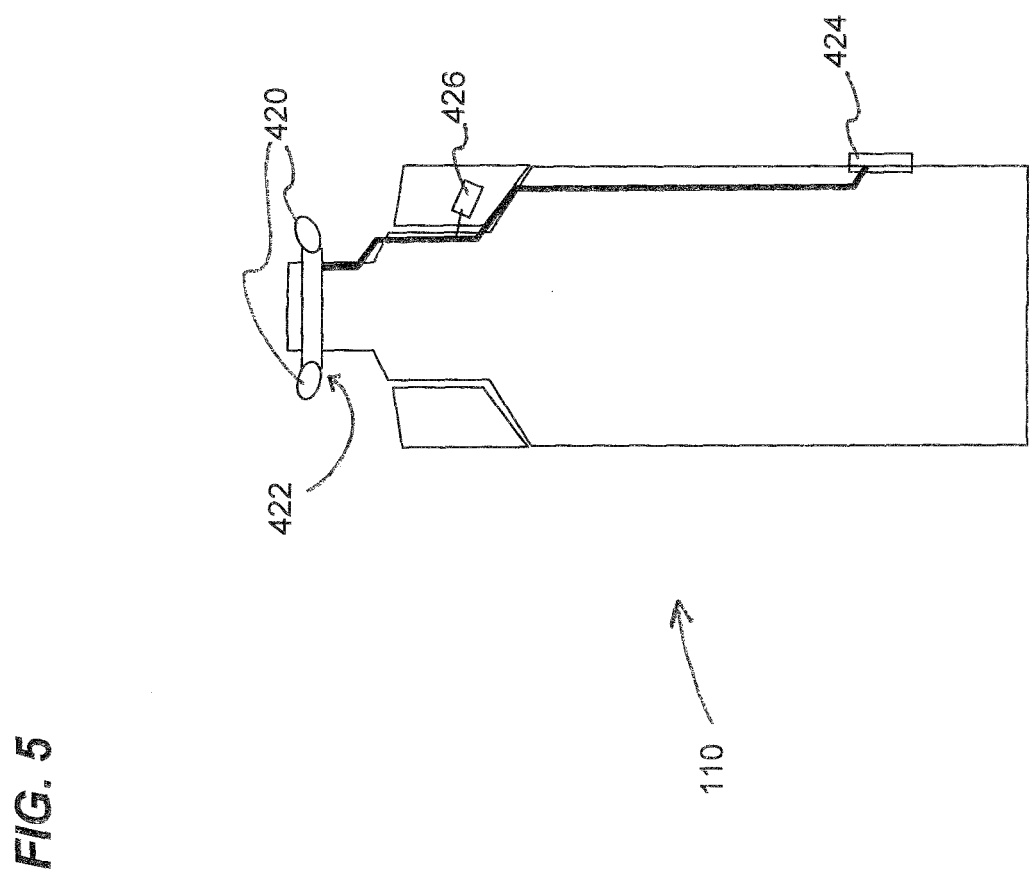
FIG. 5 is a conceptual top plan view of a medical procedure mat providing patient entertainment and communication, according to one embodiment.

FIG. 5 is a conceptual top plan view of a medical procedure mat 110 providing patient entertainment and communication capabilities, according to one embodiment. This embodiment of the mat 110 includes one or more speakers 420, as shown in the figure, to provide audio signals to the patient as desired. In some embodiments, the mat 110 may further provide a microphone 422 (which may be integrated into the speaker enclosure, for example). The speaker 420 and microphone 422 may be cleanable and movable (e.g., drop down). As shown in FIG. 5, the speaker 420 and/or microphone 422 would typically be coupled to or disposed near the head of the outer edge portion. The patient may use the microphone 422 to communicate with medical personnel, while the speakers 420 may allow the patient to hear instructions or other information provided to the patient. In some embodiments of the invention, the patient may have the ability to listen to music on the speakers 420. In one embodiment, a headset (not shown) may alternatively be used by the patient. As is shown in FIG. 5, a communications center 424 and communications center controller 426 may be provided to control a music player and/or communication system (e.g., incorporated within communications center 424). For example, a patient may use the controller 426 to control volume, music selections, and the like. For instance, if a CD player, an MP3 player, or other music/entertainment source is installed or connected, the patient may use the communications center controller 426 to select a CD (or a particular music track or entertainment track) to be played. A nurse call button or activator may also be incorporated into the communications center controller 426, according to some embodiments of the invention. In some embodiments, the communications center controller 426 may be able to send a signal to a remote monitoring station (e.g., a nurses station) in response to nurse call signal or some other alarm condition. In some embodiments, a hub 240 in the mat 110 may include an audio input connection to allow an audio signal to be transmitted to one or more speakers 420 located near the head of the outer edge portion (and hence, near the patient's head). The audio signal may be transmitted to the speakers 420 using a conductor housed within a conduit 250, according to some embodiments of the invention.

Figure 6:
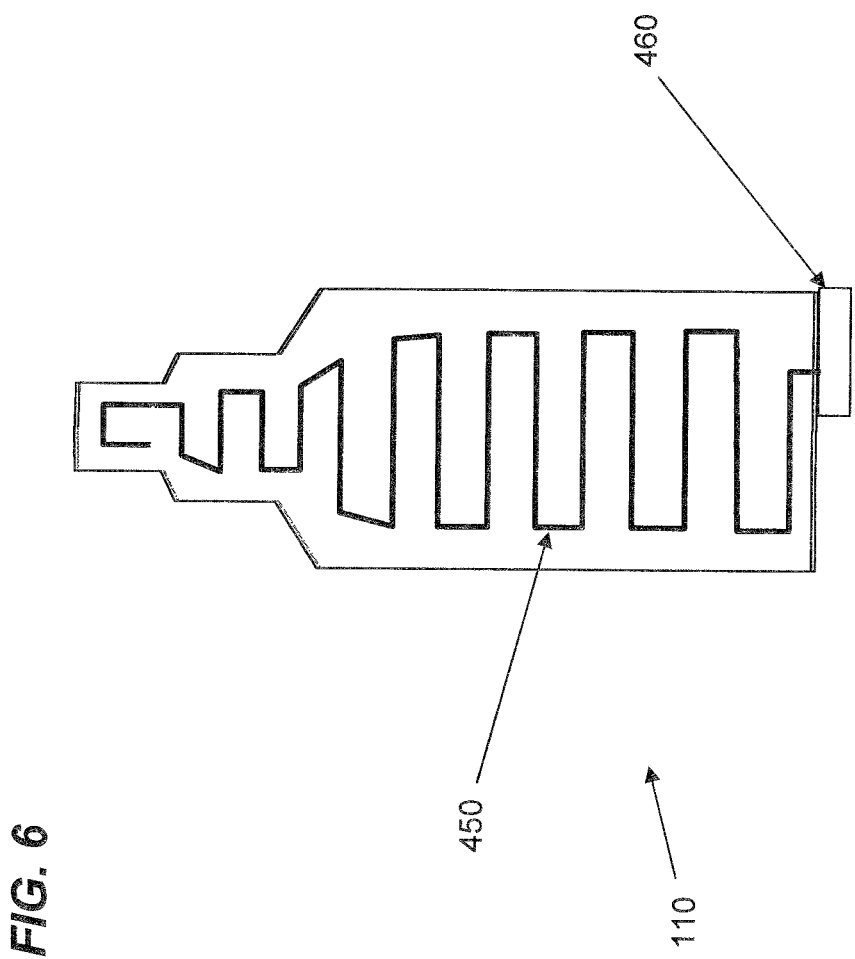
FIG. 6 is a conceptual top plan view of a medical procedure mat having a heated pad, according to one embodiment.

FIG. 6 is a conceptual top plan view of a medical procedure mat 110 having a heated pad, according to one embodiment. In this embodiment, a heater 460 is provided (as shown), as well as a radiolucent mat with a heating and ventilation system 450. Such a mat 110 can improve patient comfort, and can also reduce the need for warmed blankets. It may also facilitate the use of the mat 110 during patient recovery. In one embodiment, heating or warming may be achieved through the use of electricity, such as by using electrical coils or other heating elements (for example). In one embodiment, heating or warming may be achieved through the use of forced air. In different embodiments, various other forms of energy or stimulating for heating/warming may be used.

Figure 7:
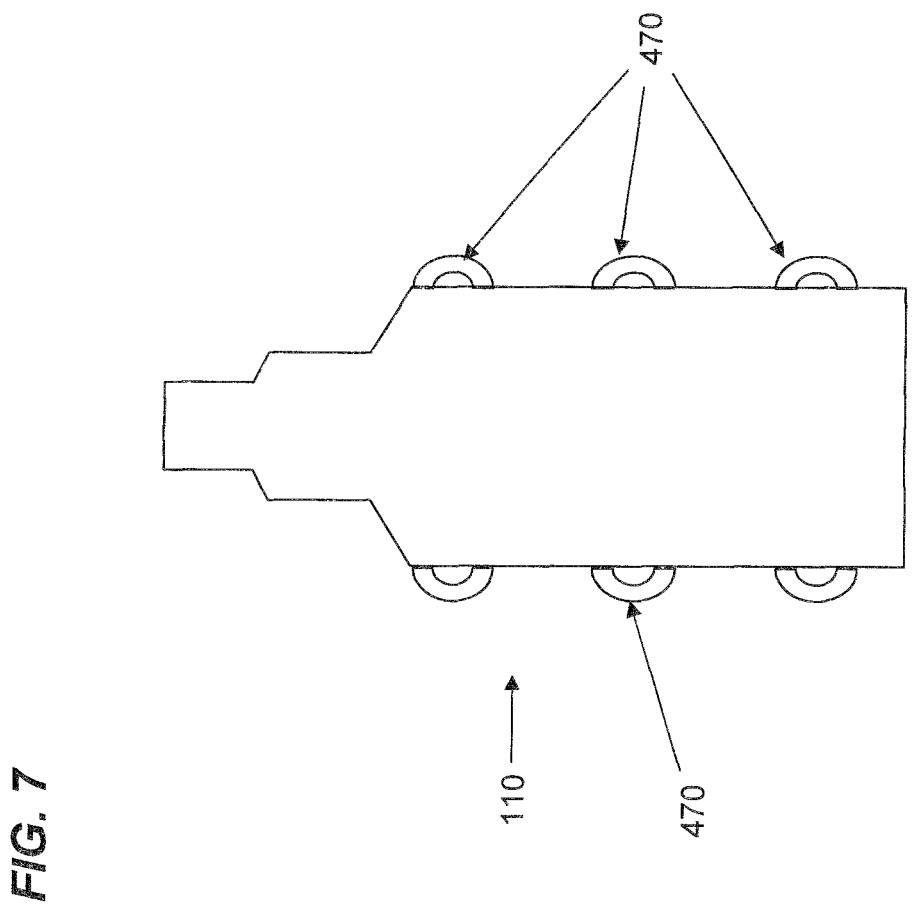
FIG. 7 is a conceptual top plan view of a medical procedure mat having handgrips for easy patient transport, according to one embodiment.

FIG. 7 is a conceptual top plan view of a medical procedure mat 110 having one or more handles or handgrips 470 to facilitate patient transport, according to one embodiment. In the embodiment shown in FIG. 7, the mat 110 may include a plurality of handgrips 470, and may include handgrips 470 on both the left and right sides of the mat 110. Handles or handgrips 470 may be coupled to the outer edge portion of mat 110, or of the cushioned substrate of mat 110. Medical personnel may use the handgrips 470, for example, to transport the patient and mat 110 onto a gurney when moving the patient from the medical procedure room to a recovery room. In certain embodiments, it is contemplated that the mat 110 will travel with the patient, rather than staying within the medical procedure room for use by various different patients. The use of handles or handgrips 470 may facilitate the use of mat 110 in this manner.

In some embodiments, additional functionality and/or capabilities may be provided by mat 110. For example, in embodiments in which the mat 110 stays with a given patient (e.g., a mat 110 with handgrips 470 that may travel with the patient from the medical procedure room to a recovery room), one or more detectors or alarms may be incorporated into mat 110, for example, to detect patient bleeding or other conditions. In some embodiments, the mat 110 may receive a signal from a sensor adapted to sense patient bleeding, and may provide an alert signal in response to a detected bleeding condition.

In some embodiments, a patient bleeding sensor may include a skin patch adapted to detect bleeding, for example, by detecting extravasation at an insertion point on the patient, or by detecting a strain signal at the insertion point by stretching of the skin patch. Examples of skin patches that detect extravasation at an insertion point by monitoring changes in impedance are provided in U.S. Pat. Nos. 5,947,910 and 5,964,703, the contents of which are incorporated by reference herein. The alert signal provided in response to a detected bleeding condition may be provided at the mat 110 itself (e.g., via audible alarm, or lights, or other cues), and/or it may be transmitted to a remote monitoring station, such as a nurses station, which may be helpful during patient recovery, for example. With reference back to FIGS. 3a-3d, a physiological monitoring line 200 may be provided with mat 110 to communicate a signal from the patient bleeding sensor to a monitoring device, for example.

Wireless ECG may also be provided, according to some embodiments of the invention. In addition, Doppler may be implemented or used for pedal pulse monitoring of the patient. In some embodiments, the mat 110 having detectors and/or alarms may stay within the medical procedure room, and would not necessarily travel with the patient.

Various embodiments of a medical procedure mat are contemplated herein. Certain embodiments include one or more features that are shown in FIG. 2 through FIG. 7, either alone or in combination. Certain embodiments also provide a drape or draping system, such as those shown in FIG. 8 through FIG. 10 and described in more detail below. Some embodiments of the drape or draping system include a top drape and a bottom drape, either alone or in combination.

Figure 8A:
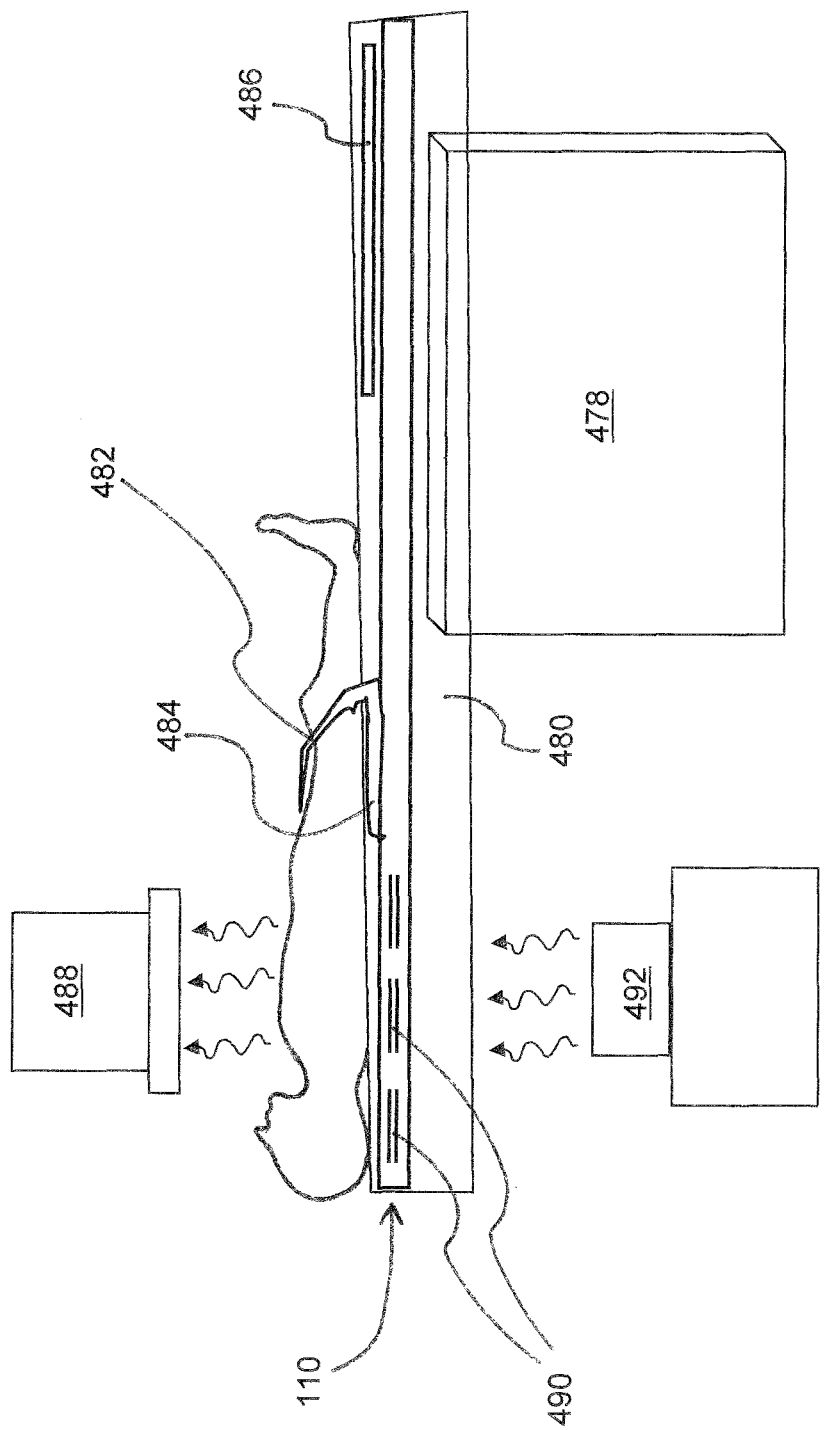
FIG. 8a is a cross-sectional side view of a medical procedure room having a table, mat, and draping system, according to one embodiment.

FIG. 8a is a cross-sectional side view of a medical procedure room having a medical procedure table 478, mat 110, and draping system, according to one embodiment. In the example shown, a patient lies on the table 478 within the room and is exposed to X-ray radiation, such as for a diagnostic or therapeutic procedure. The X-ray equipment (e.g., C-arm) may include a collimator 492 and an image intensifier 488, for example. The patient may lie on any embodiment of the mat 110 previously described (or on a mat including a combination of features from various embodiments described herein). In addition, a draping system may be used. As shown in FIG. 8, the draping system or drape may include a bottom drape 480 having a top surface and a bottom surface, and may be placed beneath the patient and on top of the mat 110. The bottom drape 480 may be used in place of a sheet, for example.

The bottom drape may include two or more holes or vents 490, which may allow for passage of physiological monitoring lines therethrough. For example, a physiological monitoring line 200, such as an ECG cable, may pass from the mat 110 to a location above the top surface of the bottom drape 480. The holes 490 in the bottom drape 480 may be arranged or positioned such that they are generally aligned with physiological monitoring lines of the mat 100, according to certain embodiments. For example, the holes 490 may be aligned with one or more operative couplings 230 of the mat 110. In some embodiments, the bottom drape 480 may be coupled to the mat 110 (or to the cushioned substrate of the mat 110), for example, by using hook and loop fasteners positioned to facilitate alignment between the holes in the bottom drape and the operative couplings of the mat 110.

In some embodiments, a bottom drape 480 may also include an absorbent material portion 484 to capture patient bodily fluids, such as urine, and/or medical procedure fluids (e.g., contrast solution, saline, etc.). The absorbent material portion 484 may be made of a material similar to that used in diapers, and may be integrated into the design of bottom drape 480. Bottom drape 480 may also include a privacy shield 482 to shield a patient's private parts or bodily areas. Privacy shield 482 may be formed of a flexible material coupled to the top surface of the bottom drape 480, for example. In some embodiments, the privacy shield 482 may be positioned (e.g., using fasteners, or an adhesive, or tape) to at least partially cover the patient's private parts (e.g., groin area), for example. In the embodiment shown in FIG. 8a, bottom drape 480 may also include a workbench support surface 486, which may be a relatively flat surface and/or may be adapted to provide a stable surface or configuration on which to support a workbench or tray.

Figure 8E:
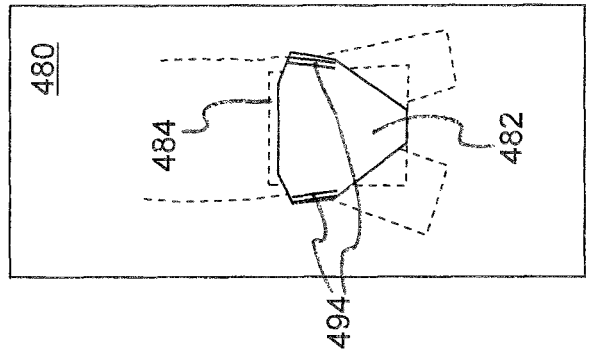
FIGS. 8b-8e are top plan views of a draping system, according to several different embodiments.
Figure 8D:
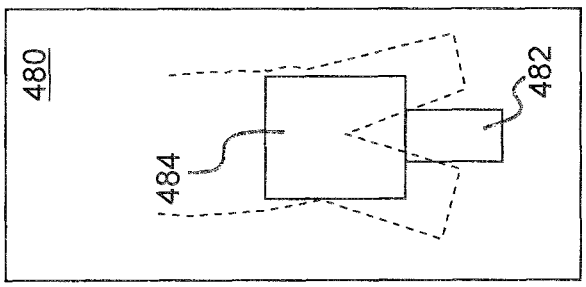
Figure 8C:
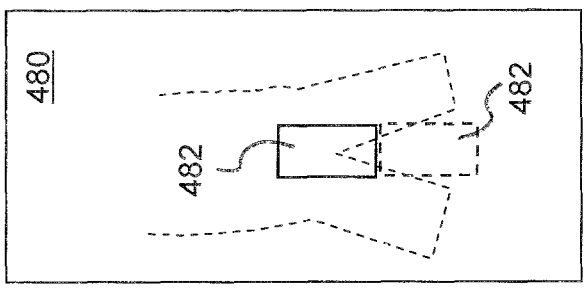
Figure 8B:
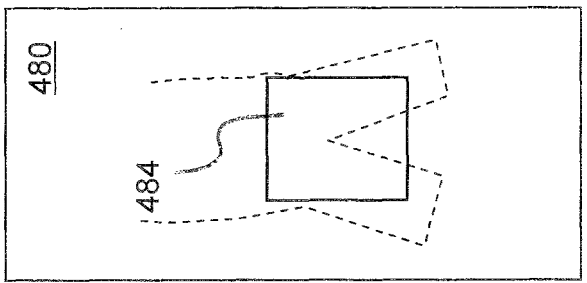

FIGS. 8b-8e show various configurations of a bottom drape 480 according to embodiments of the invention. For example, FIG. 8b shows absorbent material portion 484 incorporated into bottom drape 480. FIG. 8c shows a bottom drape 480 with a privacy shield 482 adapted to be positioned to at least partially cover a patient's groin area. FIG. 8d shows a bottom drape 480 having both an absorbent material portion 484 and a privacy shield 482. FIG. 8e shows the bottom drape of FIG. 8d with the absorbent material portion 484 positioned beneath the groin area of a patient, and with privacy shield 482 positioned over the groin area. As shown in FIG. 8e, the privacy shield 482 may be shaped to facilitate placement and coverage, and may further include fasteners 494 (e.g., hook and loop, adhesive, snaps, etc.) to maintain the positioning of privacy shield 482.

In some embodiments, the bottom drape 480 may also be capable of mating with a top drape (to be described further below with reference to FIG. 9). In one embodiment, the bottom drape may further include drape portion that is capable of being rolled in and rolled out (similar to a condom), or being otherwise extended and retracted. In this fashion, an individual outside of the medical sterile field may pass a medical instrument, such as a hand control for an injection device, to an individual within the sterile field to use during one or more medical procedures. The drape portion maintains sterility during use of the medical device. The medical device may be reused across multiple different patient procedures, but the drape portion would be a disposable component that is used for only one patient, according to one embodiment. One example of a medical device that could be reused in this fashion is a hand control, which allows a clinician to variably control the flow rate of medical fluid being injected into a patient from a powered injection system.

Figure 9:
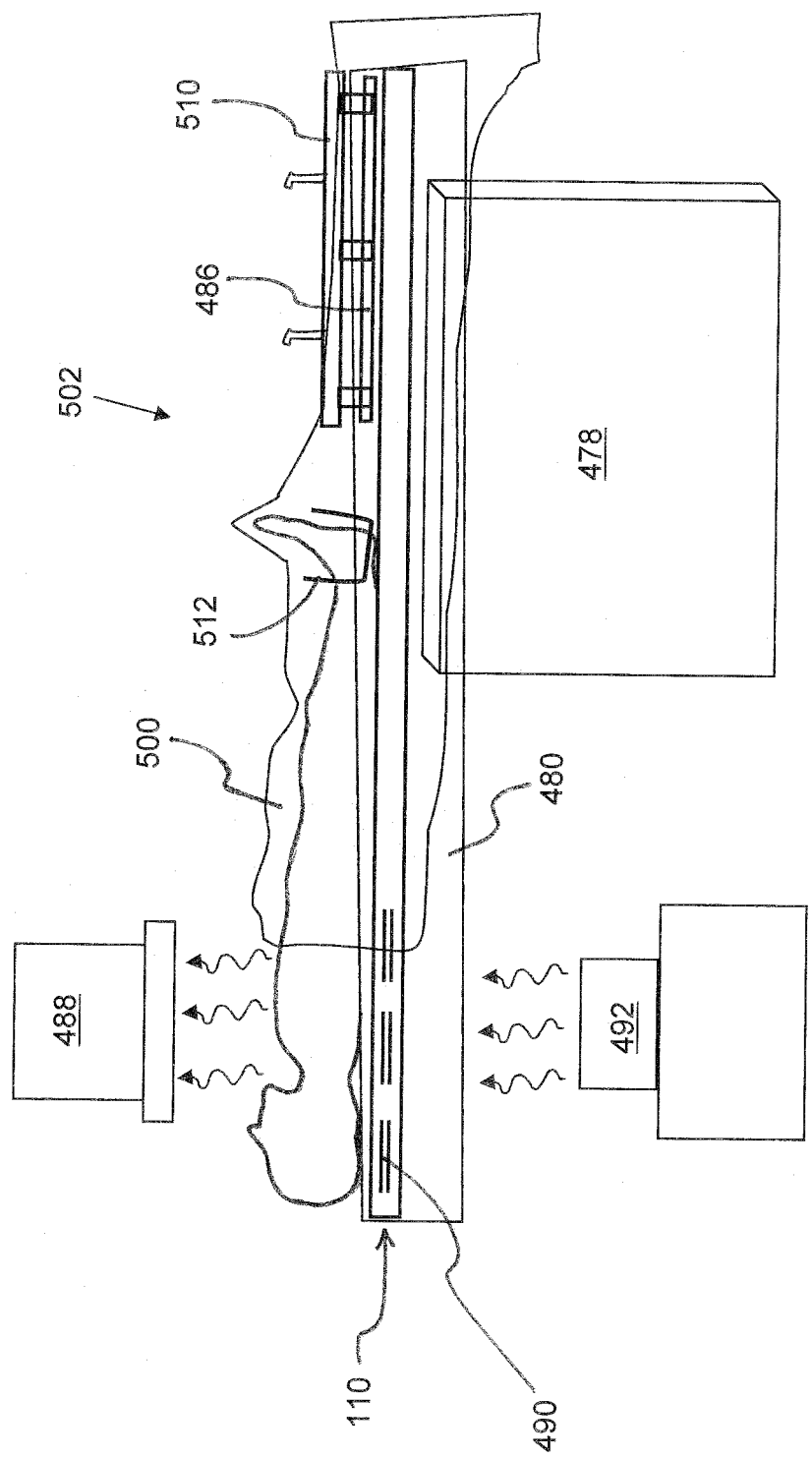
FIG. 9 is a cross-sectional side view of a medical procedure room having a table, mat, and draping system, according to one embodiment.

FIG. 9 is also a cross-sectional side view of a medical procedure room having a medical procedure table 478, mat 110, and a draping system 502, according to another embodiment. The draping system 502 of FIG. 9 includes a top drape 500 that may be mated to a bottom drape 480 of the draping system 502 to provide stability. The top drape 500 may include one or more containers 512 for holding medical procedure equipment, such as wires, balloons, or other equipment, on the table. In one embodiment, an integrated foam board 486 for a workbench 510 is provided. In one embodiment, the integrated foam board 486 of the bottom drape 480 is adapted to support a relatively flat workbench 510 to provide a stable area for placement of medical devices and equipment used during medical procedures. The surface of the workbench 510 may include some means for attaching one or more external devices to top drape 500. For example, clips may be included to hold catheters, wires, or other components during personnel exchanges. A platform may also be provided for external device or component attachment to the workbench for use by personnel during medical procedures. In one embodiment, the top drape 500 may further include a drape portion that is capable of being rolled in and rolled out (similar to a condom), or being otherwise extended and retracted, similar to that described above with respect to the bottom drape of FIG. 8a.

Figure 10:
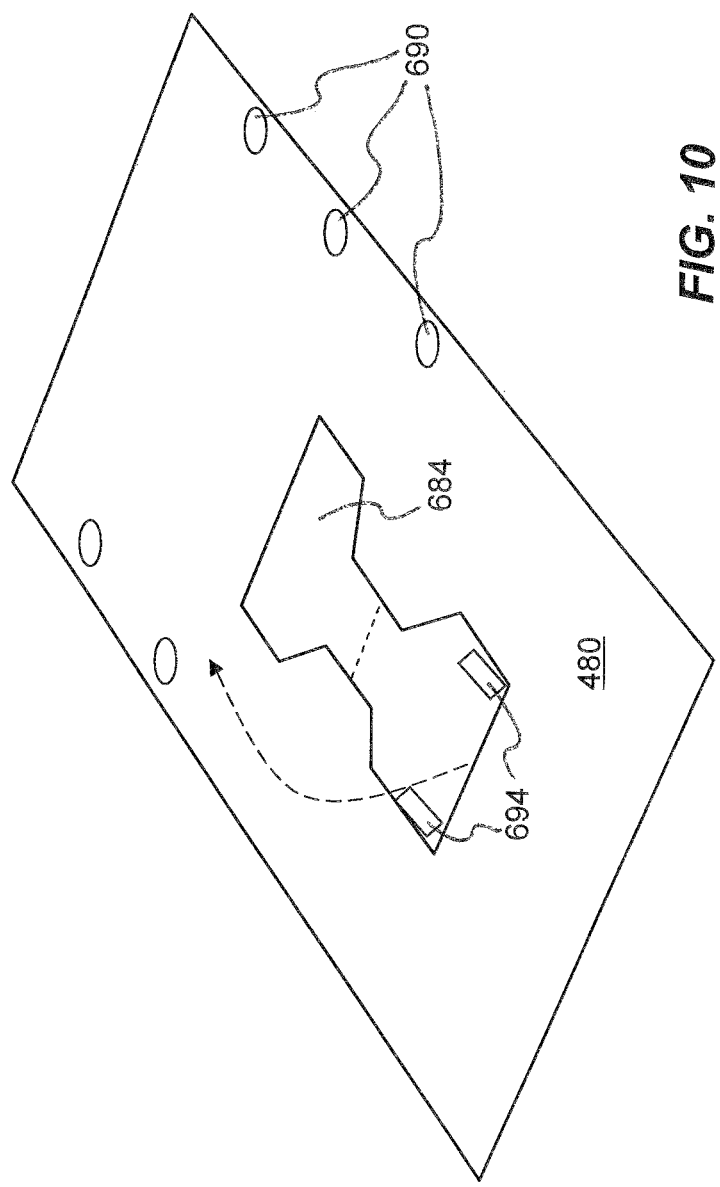
FIG. 10 is a top perspective view of a drape according to one embodiment.

FIG. 10 is a top perspective view of one embodiment of a drape. This drape may be used in the embodiments shown in FIG. 8 and FIG. 9 as part of the bottom drape 480 portion, according to one embodiment. The bottom drape 480 may include holes and/or guide channels 690, for example, to guide one or more physiological monitoring lines (such as ECG wires). Other channels may be provided for holding other tubing (such as, for example, oxygen or infusion pump tubing). In addition, a highly absorbent pad or flap 684 may be provided that goes under a patient and flips over the patient's groin area, in one embodiment. Sticky tabs 694 or other adhesive material may be used to attach the pad to the patient during a procedure and collect patient fluids, such as urine. In one embodiment, the absorbent flap 684 may be capable of holding up to one liter of fluid. By using such a pad, a patient can urinate during a procedure without worrying about urinating on the table or having to use catheterization. This may improve patient comfort during such medical procedures, and may also minimize or eliminate breaks in the procedure to clean up or catheterize the patient.

The foregoing description addresses examples encompassing the principles of various embodiments of the present invention. The embodiments may be changed, modified and/or implemented using various types of arrangements. In particular, one or more embodiments may be combined in a single mat and/or mat and draping system. Those skilled in the art will readily recognize various modifications and changes that may be made to these embodiments of the invention without strictly following the exemplary embodiments and applications illustrated and described herein, and without departing from the scope of the invention. Accordingly, it is not intended that the invention be limited, except as by the appended claims.

What is claimed is:

1. A medical procedure mat comprising:
a cushioned substrate having
a top surface for supporting a patient lying thereon,
a bottom surface adapted to be supported by a medical procedure table,
an inner portion, and
an outer edge portion comprising a head, a foot, and left and right sides; and a first physiological monitoring line for communicating a physiological signal from a physiological sensor associated with the patient, the first physiological monitoring line comprising
a guided portion having a proximal end and a distal end,
a flexible portion, and
an operative coupling between the distal end of the guided portion and the flexible portion, the operative coupling being disposed proximate the outer edge portion of the cushioned substrate;
the guided portion of the physiological monitoring line being disposed generally along the outer edge portion of the cushioned substrate,
the proximal end of the guided portion adapted to be connected to a monitoring device, and
the flexible portion being adapted to extend toward the inner portion of the cushioned substrate, further comprising at least a second physiological monitoring line wherein at least the first and second physiological monitoring lines are housed within a conduit, the conduit being disposed along the outer edge portion and within the cushioned substrate.

2. The mat of claim 1 wherein the first physiological monitoring line is adapted to communicate electrical signals.

3. The mat of claim 1 wherein the first physiological monitoring line is adapted to communicate fluid signals.

4. The mat of claim 1 wherein at least one of the first and second physiological monitoring lines is an ECG cable.

5. The mat of claim 1 wherein at least one of the first and second physiological monitoring lines is a blood pressure monitoring line.

6. The mat of claim 1 wherein at least one of the first and second physiological monitoring lines is an oxygen saturation monitoring line.

7. The mat of claim 1 wherein the conduit comprises two or more discontinuous portions.

8. The mat of claim 1 wherein the conduit is a generally annular member.

9. The mat of claim 8 wherein the annular member has a distal opening disposed proximate the operative coupling of one of the physiological monitoring lines.

10. The mat of claim 9 wherein the annular member further includes one or more side openings, each side opening being adapted to allow for operative coupling between the guided and flexible portions of one of the physiological monitoring lines.

11. The mat of claim 10 wherein one or more operative couplings are positioned on an outside surface of the cushioned substrate.

12. The mat of claim 8 wherein the annular member is a tube adapted to bend to conform to the outer edge portion.

13. The mat of claim 1 wherein the conduit comprises a hollow space formed in the cushioned substrate for guiding the guided portion of the physiological monitoring lines.

14. The mat of claim 13 wherein the outer edge portion of the cushioned substrate includes one or more side holes that extend from inside the cushioned substrate to outside the cushioned substrate.

15. The mat of claim 14 further comprising a tube disposed within the hollow space, the tube having one or more side openings generally aligned with the one or more side holes in the outer edge portion to allow the physiological monitoring lines to pass from a position inside the tube to outside the cushioned substrate.

16. The mat of claim 1 wherein the operative coupling is adapted to retract the flexible portion.

17. The mat of claim 16 wherein the operative coupling is a reel connector adapted to retract the flexible portion into a housing of the operative coupling.

18. The mat of claim 1 further comprising a first conduit disposed generally along the left side of the outer edge portion, and a second conduit disposed generally along the right side of the outer edge portion, the first and second conduits each being capable of guiding at least one of the first and second physiological monitoring lines between an area near the foot and an area toward the head of the outer edge portion.

19. The mat of claim 18 wherein the guided portion of one of the physiological monitoring lines runs from the left side to the right side near the foot of the outer edge portion.

20. The mat of claim 1 wherein the operative coupling between the guided portion and the flexible portion of the physiological monitoring lines allows the flexible portion to extend toward a physiological sensor associated with the patient.

21. The mat of claim 20 wherein at least one of the operative couplings is disposed near the head of the outer edge portion.

22. The mat of claim 1 wherein the operative coupling comprises a mechanism adapted to place a tension on the flexible portion of the physiological monitoring line to pull the flexible portion toward the operative coupling.

23. The mat of claim 22 wherein the operative coupling includes a detent position that allows an operator to selectively remove the tension placed on the flexible portion.

24. The mat of claim 1 further comprising at least one handle coupled to the outer edge portion of the cushioned substrate.

25. The mat of claim 1 wherein at least one of the physiological monitoring lines is coupled to a sensor adapted to sense patient bleeding, the mat being further adapted to send an alert signal in response to a detected bleeding condition.

26. The mat of claim 25 wherein the sensor is a skin patch adapted to detect a strain signal, and wherein the alert signal is transmitted to a remote monitoring station.

27. The mat of claim 25 wherein the sensor is a skin patch adapted to detect a change in an impedance signal, and wherein the alert signal is transmitted to a remote monitoring station.

28. The mat of claim 1 further comprising a first radiation shield, the first radiation shield being disposed along the outer edge portion of the cushioned substrate, the radiation shield being adapted to reduce scattering radiation exposure received by an operator during a patient imaging procedure.

29. The mat of claim 28 wherein the radiation shield is positionable between a stowed position and a shielding position.

30. The mat of claim 28 further comprising a second radiation shield, wherein the first radiation shield is disposed on the left side of the outer edge portion and the second radiation shield is disposed along the right side of the outer edge portion, each of the two radiation shields being selectively positionable between a stowed position and a shielding position.

31. A medical procedure mat comprising:
a cushioned substrate having
a top surface for supporting a patient lying thereon,
a bottom surface adapted to be supported by a medical procedure table,
an inner portion, and
an outer edge portion that comprises a head, a foot, and left and right sides; and
two or more physiological monitoring lines for communicating physiological signals from physiological sensors associated with the patient, each of the two or more physiological monitoring lines comprising
a guided portion having a proximal end and a distal end,
a flexible portion, and
an operative coupling between the distal end of the guided portion and the flexible portion, the operative coupling being disposed proximate the outer edge portion of the cushioned substrate, the operative coupling being adapted to retract the flexible portion;
the guided portions of the two or more physiological monitoring lines being disposed generally along the outer edge portion of the cushioned substrate,
the flexible portions of the two or more physiological monitoring lines being adapted to extend toward the inner portion of the cushioned substrate, and
the proximal ends of the guided portions being disposed near a hub adapted to facilitate connection of the physiological monitoring lines to a monitoring device,
wherein the two or more physiological monitoring lines are housed within a conduit, the conduit being disposed along the outer edge portion and within the cushioned substrate.

32. The mat of claim 31 wherein the hub comprises one or more connectors adapted to facilitate connections between the two or more physiological monitoring lines and the monitoring device.

33. The mat of claim 32 wherein the two or more physiological monitoring lines include ECG cables and wherein the monitoring device is an ECG monitor.

34. The mat of claim 31 further comprising
a first conduit disposed generally along the left side of the outer edge portion, and
a second conduit disposed generally along the right side of the outer edge portion,
the first and second conduits each being capable of guiding at least one of the first and second physiological monitoring lines between an area near the foot and an area toward the head of the outer edge portion.

35. The mat of claim 34 wherein the head of the outer edge portion is adapted to provide audio signals to the patient.

36. The mat of claim 35 wherein the hub includes an audio input connection, and wherein the first or second conduit includes an audio signal line to transmit the audio signals to one or more speakers located near the head of the outer edge portion.

* * * * *